United States Patent [19]
Chu et al.

[11] 3,963,774
[45] June 15, 1976

[54] ANILINO DERIVATIVES OF CHELOCARDIN

[75] Inventors: Daniel Tim-Wo Chu, Greenfield Park; David Lyon Garmaise, Montreal, both of Canada

[73] Assignee: Abbott Laboratories, North Chicago, Ill.

[22] Filed: Mar. 3, 1975

[21] Appl. No.: 554,849

Related U.S. Application Data

[62] Division of Ser. No. 378,305, July 11, 1973, Pat. No. 3,894,061.

[52] U.S. Cl. .............................. 260/519; 260/566 R; 424/319; 424/330
[51] Int. Cl.² ................. C07C 97/10; C07C 101/48
[58] Field of Search ....................... 260/519, 566 R

[56] References Cited
OTHER PUBLICATIONS

Mitscher, et al., Journal of the American Chemical Society, vol. 92, (1970) pp. 6070 and 6071.

*Primary Examiner*—Richard L. Raymond
*Attorney, Agent, or Firm*—Paul D. Burgauer; Robert L. Niblack

[57] ABSTRACT

A number of specific anilino derivatives of chelocardin having high antibiotic activity are described. These new derivatives show unusually low toxicity and consequently a very high therapeutic index as chemotherapeutic agents against gram-negative organisms.

3 Claims, No Drawings

ANILINO DERIVATIVES OF CHELOCARDIN

This is a division, of application Ser. No. 378,305 filed July 11, 1973, now U.S. Pat. No. 3,894,061.

DETAILED DESCRIPTION OF THE INVENTION

Chelocardin is the name assigned to the antibiotic M-319 originally described in U.S. Pat. 3,155,582 issued in 1964. The original publication did not disclose the chemical structure, but since then, the structure has been elucidated (see J.A.C.S., 92, page 6070 of 1970) and as a result of this knowledge, new derivatives were prepared. Unfortunately, predicting physiological activity of such new derivatives is impossible, but surprisingly, a new group of compounds have now been found that share and even exceed the chemotherapeutic activity of chelocardin itself while showing some advantageous physical and/or chemical properties.

The new compounds which are the subject of the present invention are the anilino and substituted anilino derivatives of chelocardin, having the following general structure:

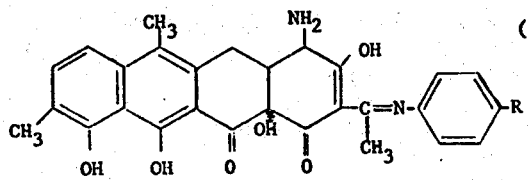

wherein R stands for hydrogen, carboxymethyl, or carboxy, or nontoxic acid addition salts thereof, or the corresponding tautomeric forms thereof.

The new compounds can easily be prepared by reacting chelocardin with a slight excess of a molar equivalent of the desired compound of the formula:

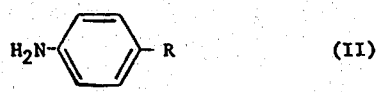

wherein R has the above meaning, in an inert, organic solvent or an aqueous mixture therewith. The term "inert" is used herein to express that the solvent does not react or interfere with any of the starting materials or the formed end product. A preferred reaction medium is aqueous tetrahydrofuran (hereinafter simply referred to as THF) wherein the THF contains between 0.1 to 5 percent by volume of water. However, good results are also obtained when the reaction medium is methanol, ethanol or the like. Usually, it is preferred to react the suitable solvent of chelocardin with the desired anilino compound of formula II.

In a preferred embodiment, a nontoxic acid addition salt of chelocardin or chelocardin itself is combined with the compound of formula II in an inert, organic solvent and the solution is allowed to stand for at least 1 hour at room temperature. Reaction times beyond 24 hours usually add no further benefit and in most instances, the condensation is essentially complete in 1 – 8 hours. If desired, the temperature of the reaction medium may be raised but since room temperature is usually adequate, no need exits to heat the mixture beyond 70° C. A preferred reaction solvent is THF containing 5% of water. If chelocardin base is the starting material, the condensation product of formula I is obtained. If the starting material is an acid addition salt, the final product is the corresponding acid addition salt of the compound of formula I. In either case, the base can easily be converted to the desired salt and the salt can easily be converted to the base in routine and known fashion.

In order to illustrate the manner of preparing the new compounds, reference is made to the following examples which, however, are not intended to limit the invention in any respect. In all instances, the thin-layer and spectrographic data obtained were in agreement with the assigned structures. The new p-substituted aniline moieties were always found in the 2α-position of chelocardin; these structural positions are not repeated in the following examples as they are clearly indicated through formula I.

EXAMPLE 1

A solution of 0.3 g. of acetic acid in 5 ml. of THF is added to 1 g. of chelocardin hydrochloride dissolved in 40 ml. of 95% aqueous THF. A solution of 0.3 g. of aniline dissolved in 5 ml. of THF is then added and the mixture, after being stirred at room temperature for 18 hours, is condensed under reduced pressure to a volume of 5 ml. This concentrated solution is mixed with 5 ml. of ethanol and the solution is then added slowly into a stirred solution of 250 ml. of ether. The resulting suspension is filtered and the residue is washed twice with ether in portions of 20 ml. each, yielding 1.1 g. (96% of theory) of anilino-chelocardin hydrochloride.

EXAMPLE 2

A solution of 0.15 g. of acetic acid in 1 ml. of THF is added to a solution of 0.46 g. of chelocardin hydrochloride in 8 ml. of 95% aqueous tetrahydrofuran. To this mixture is added 0.17 g. of p-carboxymethylaniline and after stirring this mixture at room temperature for 3 hours, it is slowly added to a stirred solution of 200 ml. of ether. The suspension is filtered and the residue is washed twice with 20 ml. portions of ether, yielding 391 mg. (90%) of p-carboxymethylanilino-chelocardin hydrochloride.

EXAMPLE 3

A solution of 150 mg. of acetic acid in 1 ml. of THF is added to 400 mg. of chelocardin hydrochloride suspended in 15 ml. of THF. After adding 150 mg. of p-aminobenzoic acid, the mixture is stirred at room temperature for 5 days. 20 ml. of ether is then added and the suspension is filtered and the residue is washed twice with 20 ml. portions of ether, yielding 430 mg. (84%) of p-carboxyanilino-chelocardin hydrochloride.

EXAMPLE 4

In order to show the antibiotic and bacteriostatic activity of the compounds of the present invention, the minimum inhibitory concentrations (MIC) are demonstrated in Table I below. The bacteria are first grown in a brain-heart infusion broth for 24 hours at the optimum temperature for the organism. The culture is then diluted with water so that there are about 10 Mio. viable organisms per milliliter. The cell suspension is used as the inoculum of the tests reported below. The test compounds, about 20 mg. of each, are dissolved in 0.2 ml. of methanol and 19.8 ml. of water. The various test solutions of varying concentrations are well distributed in agar suspensions adjusted to a pH of 7.4 and placed in Petri dishes so that each dish contains a known amount of test compound.

The surfaces of the solidified agar plates are then inoculated with the test culture by streaking the test culture on the surface of the plate with a standardized loop that has been dipped in the inoculum and incubated at room temperature for 24 hours. The MIC values in Table 1 are expressed in mcg./ml.

TABLE 1

| Compd. of Ex. | Staph. Aureus 45 | Staph. Aureus Smith | S. Pyo- genes C-203 | Entero- coccus 89 | Escher. Coli Juhl | Kleb. Pneum. 8045 | Past. Mult. 10544 | Pseudo. Aerugi BMH No. 10 | Prot. Vulg. ABB JJ | Prot. Mira. Fin. 9 | Salm. Typhi. Ed. 9 | D. pneumon. 6301 |
|---|---|---|---|---|---|---|---|---|---|---|---|---|
| 1 | 12.5 | 12.5 | 12.5 | 25 | 25 | 12.5 | 1.56 | >100 | 6.2 | 6.2 | 6.2 | 25 |
| 2 | 12.5 | 12.5 | 3.1 | 6.2 | 25 | 3.1 | 0.78 | >100 | 3.1 | 6.2 | 3.1 | 12.5 |
| 3 | 6.2 | 3.1 | 3.1 | 6.2 | 6.2 | 1.56 | 0.35 | 50 | 1.56 | 3.1 | 1.56 | 6.2 |

As shown in Table 1, the compounds of the present invention exhibit valuable bacteriostatic properties and are consequently useful in pharmaceutical compositions. The compounds of this invention also exhibit very low oral and subcutaneous toxicities and produce generally the same antibiotic activities in vivo as chelocardin.

In addition to the excellent bacteriostatic properties of the new compounds, they also show a surprising physical characteristic: they are more soluble in water than chelocardin and therefore, the new compounds distinguish favorably over chelocardin itself. The excellent solubility makes the new compounds particularly suitable for parenteral solutions which can easily be prepared by simply dissolving the new chelocardin derivatives in water which may be buffered to a pH of 7.0 to 7.8 and may contain 0.5 – 5% by weight of a preservative such as benzyl alcohol.

Preferably, the new derivatives are used in the form of their acid addition salts with pharmaceutically acceptable acids, i.e., hydrochloric, sulfuric, acetic, phosphoric, tartaric, citric or succinic acid. Since the hydrochloric acid forms stable acid addition salts with the new compounds and such salts are suitable for pharmaceutical preparations can be easily prepared, they are preferred.

For oral dosage forms, tablets, pills, wafers, suspensions, syrups, etc. can be prepared in standard fashion using the usual pharmaceutically acceptable excipients such as carriers, diluents, pigments, dyes and coatings. The coatings for tablets may be of the kind that dissolves rapidly in the acidic environment of the stomach, or a sustained-release coating formulation may be selected to provide a gradual release of the active ingredient over an extended period of time in order to maintain a bacteriostatic blood level over periods ranging from 2 – 24 hours.

For the treatment of smaller animals, a daily dose of 10 – 200 mg./kg. is recommended for oral administration. For larger animals, including humans, a daily oral dose of 50 – 800 mg./day produces a desirable antibiotic activity. Oral dosages are preferably prepared in unit dosage form with the dosage selected in such amounts that a single or several doses are administered over a 24 hour period.

What is claimed is:

1. A compound of the formula:

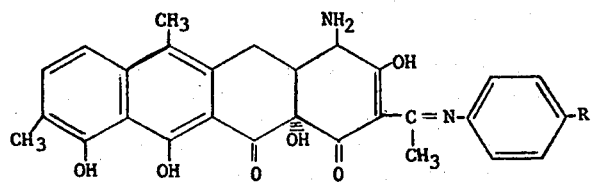

wherein R is hydrogen, carboxymethyl, or carboxy, or the corresponding tautomeric forms or a pharmaceutically acceptable acid addition salt thereof.

2. The compound of Claim 1 wherein R is carboxy.

3. The compound of Claim 1 wherein R is carboxymethyl.

* * * * *